United States Patent [19]

Schrader et al.

[11] Patent Number: 4,927,627

[45] Date of Patent: May 22, 1990

[54] EMULSION-FORM HYDROGEN PEROXIDE PREPARATIONS FOR THE BLEACHING AND OXIDATIVE DYEING OF HAIR

[75] Inventors: Dieter Schrader, Duesseldorf; Winifried Neuhaus, Mettmann, both of Fed. Rep. of Germany

[73] Assignee: Henkel Kommanditgesellschaft auf Aktien, Duesseldorf, Fed. Rep. of Germany

[21] Appl. No.: 248,875

[22] Filed: Sep. 23, 1988

[30] Foreign Application Priority Data

Sep. 24, 1987 [DE] Fed. Rep. of Germany ....... 3732147

[51] Int. Cl.$^5$ .................. A61K 7/135; A61K 7/13
[52] U.S. Cl. ................. 424/62; 424/DIG. 3; 8/406; 514/938
[58] Field of Search ............... 424/62, DIG. 3; 252/174.24, 95, 103, 186.29, 186.41, 186.43; 514/938, 943; 8/406, 431

[56] References Cited

U.S. PATENT DOCUMENTS

| | | | |
|---|---|---|---|
| 3,122,417 | 2/1964 | Blaser et al. | 23/207.5 |
| 3,130,164 | 4/1964 | Best | 252/99 |
| 3,912,446 | 10/1975 | Zuzk et al. | 424/62 X |
| 3,919,102 | 11/1975 | Kühling et al. | 252/95 X |
| 4,079,015 | 3/1978 | Pzucot et al. | 252/95 |
| 4,496,473 | 1/1985 | Sanderson | 424/62 X |
| 4,685,931 | 8/1987 | Schieferstein et al. | 8/406 |

FOREIGN PATENT DOCUMENTS

| | | |
|---|---|---|
| 0092932 | 11/1983 | European Pat. Off. . |
| 216334 | 1/1987 | European Pat. Off. . |
| 0216334 | 4/1987 | European Pat. Off. . |
| 0716197 | 12/1941 | Fed. Rep. of Germany . |
| 1164095 | 2/1964 | Fed. Rep. of Germany . |
| 1902261 | 9/1969 | Fed. Rep. of Germany . |
| 3534471 | 4/1987 | Fed. Rep. of Germany . |
| 2182781 | 12/1973 | France . |
| 2303075 | 10/1976 | France . |
| 0387211 | 7/1958 | Switzerland . |
| 870994 | 6/1961 | United Kingdom . |

*Primary Examiner*—Ellis P. Robinson
*Assistant Examiner*—Susan Rucker
*Attorney, Agent, or Firm*—Ernest G. Szoke; Wayne C. Jaeschke; Norvell E. Wisdom, Jr.

[57] ABSTRACT

Emulsion-form hydrogen peroxide compositions in the form of an oil-in-water emulsion containing oil or fatty components, emulsifiers and hydrogen peroxide and, in addition, a thickening agent comprising a carboxyl-group containing polymer or copolymer soluble in aqueous alkali in a quantity of from about 1 to about 5% by weight solids, based on the weight of the composition. These compositions are particularly suitable as an oxidizing component in processes for the dyeing or lightening of hair resulting in improved depth of color and brightness.

25 Claims, No Drawings

EMULSION-FORM HYDROGEN PEROXIDE PREPARATIONS FOR THE BLEACHING AND OXIDATIVE DYEING OF HAIR

BACKGROUND OF THE INVENTION

1. Field of the Invention

This invention relates to emulsion-form compositions containing hydrogen peroxide which are particularly suitable as components of oxidizing preparations for the bleaching of hair and for the dyeing of hair with oxidation hair dyes.

2. Description of Related Art

The bleaching and dyeing of hair with oxidation hair dyes is normally carried out with two separately packed preparations, the bleaching cream or oxidation hair dyeing cream (A) and the oxidizing preparation (B), which are combined and mixed shortly before application and then applied to the hair as a ready-to-use bleaching or dyeing preparation. Dual-compartment mixing and dispensing containers have also been developed for home use, in which components A and B are packed separate from one another in a suitable quantitative ratio. Such containers comprise a partition which is mechanically destructible from outside positioned between the two compartments and a dispensing opening in one of the two compartments. Just before application, the partition is ruptured by the user after which components A and B are combined and mixed by shaking or by other mechanical means. The ready-to-use hair dye or bleaching preparation may then be removed from the dispensing opening and applied directly to the hair.

It has been found to be advantageous to formulate both the hair dyeing or bleaching cream (A) and the oxidizing preparation (B) in the form of a water-in-oil emulsion, especially for application using the dual-compartment container referred to above. This facilitates rapid and homogeneous mixing of the oxidation preparation with the hair dyeing or bleaching cream. This approach, which is described in German patent document 35 34 471, has been found to have the disadvantage in that the colors obtainable in this way have relatively little depth of color and evenness, and the bleached finishes are dull.

DETAILED DESCRIPTION OF THE INVENTION

Other than in the operating examples, or where otherwise indicated, all numbers expressing quantities of ingredients or reaction conditions used herein are to be understood as modified in all instances by the term "about".

The present invention provides hydrogen peroxide emulsions for use in hair dyeing or bleaching compositions which exhibit improved depth of color and brightness as compared with prior art preparations. The formulations of this invention are in the form of an oil-in-water emulsion containing an oil or fatty component, an emulsifier and hydrogen peroxide. The emulsion further contains a thickening agent comprising a carboxyl-group-containing polymer or copolymer soluble in aqueous alkali and present in a quantity of from 1 to 5% by weight solids, based on the total weight of the formulation.

The preferred carboxyl-containing polymers and copolymers used in this invention are polymers or copolymers of acrylic acid or methacrylic acid. Such polymers and copolymers are known in the prior art and have been used a thickeners for aqueous solutions. British patent 870,994 discloses dispersions of copolymers comprising at least 10% by weight of a lower alkyl ester of acrylic acid, 25 to 70% by weight of methacrylic acid and, optionally, 0 to 40% by weight of another comonomer, said dispersions having a solids content of 25 to 50% by weight. German patent, document 11 64 095 discloses copolymers comprising 50 to 75% by weight of ethyl acrylate, 25 to 35% by weight of acrylic acid and 0 to 25% by weight of other comonomers. The molecular weight and hence the thickening effect of such copolymers may be modified by the addition of cross-linking, polyunsaturated copolymerizable comonomers. Particularly effective acrylate dispersions are disclosed in U.S. Pat. No. 4,685,931.

The carboxyl-containing polymers suitable for use in accordance with the invention are in the form of aqueous dispersions having a solids content of 20 to 30% by weight, which are stable and of low viscosity at a pH range of about 2 to 5. The pH value of such a dilute solution is raised by mixing the solution with an aqueous base such as alkali hydroxide solutions, including solutions of sodium hydroxide or potassium hydroxide, ammonia solution, and alkanolamines, including mono- di- or thriethanolamines. The carboxyl groups are consequently converted into the salt form, which permits the polymer chains to uncoil and pass into solution with the result that the aqueous solution exhibits an increase in viscosity. The complete ionization of the carboxyl groups, the development of desired viscosity, and clear water solubility are achieved at a pH value of approximately 8.

The hydrogen peroxide preparation according to the invention is in the form of an oil-in-water emulsion with a discontinuous oil or fatty phase and a continuous aqueous phase. The viscosity of this oil-in-water emulsion may be controlled within wide limits by means of the ratio of oil phase to aqueous phase or by means of the type of fatty components used. The preferred viscosity of the hydrogen peroxide preparation according to this invention is a value of from 0.5 to 2 Pa.s, as measured at 20° C. and at a shear rate (D) of 3 to 6 $cm^{-1}$, and the preferred pH value is in the range of 3 to 5, the most preferred pH being 4.

The oily or fatty component present in the hydrogen peroxide preparation may include paraffin waxes, vaseline, waxes, hard fats, cosmetic oil components, fatty alcohols, and mixtures thereof. Saturated $C_{12}$–$C_{22}$ fatty alcohols are preferred as the fatty component.

Anionic, zwitterionic, and nonionic surfactants or mixtures thereof may be used as emulsifiers. Suitable anionic surfactants which may be used include those containing an alkyl group, preferably linear, containing 12 to 18 carbon atoms and having an anionic group attached thereto such as a —$COO^{(-)}$—, $SO_3^{(-)}$— or —O—$(C_2H_4O)_x$—$SO_3^{(-)}$— group, wherein X is 0 or a number of from 1 to 20. Nonionic surfactants suitable as emulsifiers include adducts of 2 to 30 mol ethylene oxide with $C_{12}$–$C_{18}$ fatty alcohols, with alkyl phenols containing 8 to 15 carbon atoms in the alkyl group, with $C_{12}$–$C_{18}$ fatty acids, with glycerol fatty acid ($C_{12}$–$C_{18}$) partial esters, with sorbitan fatty acid ($C_{12}$–$C_{18}$) partial esters, with $C_{12}$–$C_{18}$ fatty amines, with fatty acid ($C_{12}$–$C_{18}$) monoethanolamide or with alkyl ($C_{12}$–$C_{18}$) glucosides.

Suitable zwitterionic surfactants include N-$C_{12}$–$C_{18}$-alkyl-N,N-dimethylammonioglycinate, N-$C_{12}$–$C_{18}$- acylaminopropyl-N,N-dimethylammonioglycinate or 2-(N-$C_{12}$-$C_{18}$-alkyl-N,N-dimethylammonio)-propionate. In a preferred embodiment, the hydrogen peroxide preparations according to the invention are oil-in-water emulsions of the following compositions:

(a) 1 to 5% by weight of a fatty component comprising a saturated $C_{16}$-$C_{22}$ fatty alcohol;

(b) 1 to 10% by weight of an emulsifier selected from the group consisting of a fatty alcohol ethoxylate of the formula $R^1$—$O(C_2H_4O)_n$—H, an alkyl sulfate or alkyl ether sulfate of the formula $R^1$—$O(C_2H_4O)_m$—$SO_3^{(-)}M^{(+)}$, and mixtures thereof, wherein $R^1$ is a $C_{12}$-$C_{18}$ alkyl group, n is an integer of 2 to 30, m is 0 or 1 to 30, and $M^{(+)}$ is selected from the group consisting of alkali-, $NH_4^{(+)}$, $\frac{1}{2} Mg^{(++)}$ and a mono-, di- or trialkanolammonium ion containing 2 or 3 carbon atoms in the alkanol group;

(c) 1.5 to 15% by weight hydrogen peroxide;

(d) 1 to 5% by weight of a thickening agent comprising an acrylic or methacrylic acid polymer or copolymer soluble in aqueous alkali; and (e) 65 to 95.5% by weight water.

In addition to components (a) through (e), the hydrogen peroxide preparations of the invention may also contain other auxiliaries in small quantities as follows:

(f) 0.05 to 1.5% by weight of one or more stabilizers for hydrogen peroxide, including dipicolinic acid, quinolinic acid, polyphosphates or the acylation products of phosphorous acid such as disclosed in U.S. Pat. No. 3,122,417, preferably 1-hydroxyethane-1,1-diphosphonic acid.

(g) one or more buffers for adjusting the pH value of the preparation to from 3 to 5, with acidic sodium pyrophosphate ($Na_2H_2P_2O_7$), being the preferred buffer;

(h) one of more active hair-cosmetic components, including water-soluble protein derivatives and water-soluble cationic polymers; and (i) perfumes.

The oxidation hair dyeing cream which may be mixed with the hydrogen peroxide emulsion is also an oil-in-water emulsion containing oil or fatty components, emulsifiers and oxidation hair dye precursors. The preferred pH value of the emulsion is in the range of 8 to 11, with the preferred pH being 9.5, and the viscosity is preferably adjusted to a value of 5 to 20 Pa.s, as measured at 20° C. and at a shear rate of 3 to 6 $cm^{-1}$ (1 Pascal second-Pa.s-approximates 1000 centipoise-cp.)

The bleaching cream which may be mixed with the hydrogen peroxide emulsion has a composition similar to the oxidation hair dyeing cream referred to above, and has the same pH and viscosity criteria. However, it generally contains no oxidation dyes and, at most, small quantities of oxidation dye precursors. These precursors tend to compensate for excessively strong yellows and reds which may develop upon application of the bleaching cream to the hair.

The final preparation for dyeing or bleaching the hair is prepared by thoroughly mixing the hydrogen peroxide emulsions as described above and having a pH of from 3 to 5, with either the oxidation hair dyeing cream emulsion or the bleaching cream emulsion as described above, the latter components each having a pH of from 8 to 11. The resulting mixture is found to have a viscosity suitable for application to the hair as a consequence of the dissolution of the carboxyl group-containing polymer which is a component of the hydrogen peroxide emulsion. The preferred mixing ratio of the hair dyeing of bleaching cream emulsion with respect to the hydrogen peroxide emulsion is within the range of 3:1 to 1:1, with 2:1 being most preferred for the hair dyeing cream and 1:1 being most preferred for the hair bleaching cream.

The final preparation for dyeing or bleaching the hair may be then applied to the hair at room temperature and rinsed away in the normal way after a contact time of 10 to 60 minutes.

The hydrogen peroxide emulsions of the invention form homogeneous mixtures with the emulsion-form hair dyeing creams or bleaching creams with little effort and are therefore suitable for packing in the two-compartment mixing and dispensing containers referred to above. The hair colors and bleach finishes obtained with the hydrogen peroxide preparations according to the invention are distinguished by improved depth of color and brightness.

The invention is illustrated by the following Examples.

EXAMPLES 1-2

Hydrogen peroxide preparations of this invention were prepared by forming oil-in-water emulsions having the following compositions in parts by weight:

|  | EX. 1 | EX. 2 |
|---|---|---|
| Cetyl alcohol | 1.5 | 2 |
| Lauryl-/myristyl alcohol (70:30) + 2 mol EO | 3.0 | 2.0 |
| Lauryl-/myristyl alcohol polyglycol (3EO) ether sulfate, Na salt (28% solution in $H_2O$) | 8.0 | — |
| Lauryl-/myristyl alcohol polyglycol (30EO) ether sulfate, Na salt (30% solution in $H_2O$) | — | 9.0 |
| $Na_2H_2P_2O_7$ | 0.03 | 0.03 |
| Dipicolinic acid | 0.1 | 0.1 |
| 1-Hydroxyethane-1,1-diphosphonic acid | 1.5 | 1.5 |
| Latekoll ™ D (acrylic acid/ methacrylic acid copolymer, 25% dispersion in $H_2O$) | 10.0 | 15.0 |
| Hydrogen peroxide (50% by weight in $H_2O$) | 24.0 | 12.0 |
| Ammonia (25% by weight in $H_2O$) | to pH 4 | to pH 4 |
| Water | ad* 100 | ad* 100 |

*adjusted to 100 parts by weight

EXAMPLES 3-4

Oil-in-water emulsions based on typical oxidation hair dyeing creams (Example 3) and bleaching creams (Example 4) were prepared having the following compositions in parts by weight:

|  | EX. 3 | EX. 4 |
|---|---|---|
| $C_{12}$-$C_{18}$ fatty alcohol mixture | 8 | 11 |
| Oleic acid diethanolamide | — | 6 |
| $C_{16}$-$C_{18}$ fatty alcohol + 25 EO | 4 | 3 |
| $(NH_4)_2$—$SO_4$ | 0.65 | 1.0 |
| Oxidation dye precursors | 1.5 | — |
| $Na_2SO_3$ | 1.0 | — |
| 1-Hydroxyethane-1,1-diphosphonic acid | 0.1 | — |
| Protein hydrolyzate | — | 0.25 |
| Ammonia (25% by weight in $H_2O$) | to pH 9.5 | to pH 9.5 |
| Water | ad 100 | ad 100 |

To dye hair, the oxidation hair dyeing cream of Example 3 was mixed with the hydrogen peroxide preparation of Example 2 in a respective ratio of 2:1 parts by weight. A ready-to-use oxidation hair dyeing preparation was thus formed. To bleach hair, the bleaching cream of Example 4 was mixed with the hydrogen peroxide preparation of Example 1 in a respective ratio of 1:1 parts by weight. A ready-to-use bleaching preparation was thus obtained.

It is to be understood that the above described embodiments of the invention are illustrative only and that modifications throughout may occur to those skilled in the art.

We claim:

1. An oil-in-water emulsion suitable for use as a component in hair dyeing and hair bleaching preparations comprising a mixture of:
    (a) an oily component selected from the group consisting of oils, fatty alcohols, and mixtures thereof;
    (b) one or more emulsifiers selected from the group consisting of anionic, zwitterionic and nonionic surfactants, and mixtures thereof;
    (c) hydrogen peroxide;
    (d) a thickening agent selected from the group consisting of polymers and copolymers containing carboxyl groups and soluble in aqueous alkali; and
    (e) water;
    said emulsion having a viscosity within the range of about 0.5 to about 2 Pa.s as measured at 20° C. and at a shear rate of about 3 to about 6 cm$^{-1}$.

2. The emulsion of claim 1 wherein said thickening agent is a polymer or copolymer of an acrylic or methacrylic acid or lower alkyl esters thereof.

3. The emulsion of claim 2 wherein said thickening agent is present in said emulsion at a level of from about 1 to about 5% by weight solids, based on the emulsion as a whole.

4. The emulsion of claim 3 wherein said oil component is a fatty alcohol having 16 to 22 carbon atoms.

5. The emulsion of claim 4 wherein said fatty alcohol is a saturated fatty alcohol present at a level of from about 1 to about 5% by weight solids of the emulsion.

6. The emulsion of claim 5 wherein said fatty alcohol is cetyl alcohol.

7. The emulsion of claim 1 wherein said emulsifier is selected from the group consisting of a fatty alcohol ethoxylate of the formula $R^1$—$O(C_2H_4O)_n$—H, an alkyl sulfate or alkyl ether sulfate of the formula $R^1$—$O(C_2H_4O)_m$—$SO_3^{(-)}M^{(+)}$, and mixtures thereof, wherein $R^1$ is a $C_{12}$-$C_{18}$ alkyl group, n is an integer of 2 to 30, m is 0 or 1 to 30, and $M^{(+)}$ is selected from the group consisting of alkali-, $NH_4^+$, $\frac{1}{2}Mg^{(++)}$ and a mono-, di- or trialkanolammonium ion containing 2 or 3 carbon atoms in the alkanol group.

8. The emulsion of claim 7 wherein said emulsifier is present at a level of from about 1 to about 10% by weight solids of said emulsion.

9. The emulsion of claim 1 wherein said hydrogen peroxide is present at a level of from about 1.5 to about 15% by weight of said emulsion.

10. The emulsion of claim 1 having a pH within the range of from about 3 to about 5.

11. An oil-in-water emulsion suitable for use as a component in hair dyeing and hair bleaching preparations comprising a mixture of:
    (a) a fatty alcohol containing from 16 to 22 carbon atoms;
    (b) one or more emulsifiers selected from the group consisting of anionic, zwitterionic and nonionic surfactants, and mixtures thereof;
    (c) hydrogen peroxide;
    (d) from about 1 to about 5% by weight solids of a thickening agent selected from the group consisting of polymers and copolymers containing carboxyl groups and soluble in aqueous alkali; and
    (e) water 12. The emulsion of claim 11 wherein said thickening agent is a polymer or copolymer of an acrylic or methacrylic acid or lower alkyl esters thereof.

13. The emulsion of claim 12 wherein said thickening agent is a copolymer of acrylic and methacrylic acids.

14. The emulsion of claim 12 wherein said thickening agent is present at a level of from about 2 to about 4% by weight solids.

15. The emulsion of claim 11 wherein said fatty alcohol present at a level of from about 1 to about 5% by weight solids of the emulsion.

16. The emulsion of claim 15 wherein said emulsifier is present at a level of from about 1 to about 10% by weight solids of the emulsion.

17. The emulsion of claim 16 wherein said emulsifier is selected from the group consisting of a fatty alcohol ethoxylate of the formula $R^1$—$O(C_2H_4O)_n$—H, an alkyl sulfate or alkyl ether sulfate of the formula $R^1$—$O(C_2H_4O)_m$—$SO_3^{(-)}M^{(+)}$, and mixtures thereof, wherein $R^1$ is a $C_{12}$-$C_{18}$ alkyl group, n is an integer of 2 to 30, m is 0 or 1 to 30, and $M^{(+)}$ is selected from the group consisting of alkali-, $NH_4^+$, $\frac{1}{2}Mg^{(++)}$ and a mono-, di- or trialkanolammonium ion containing 2 or 3 carbon atoms in the alkanol group.

18. The emulsion of claim 15 wherein said hydrogen peroxide is present at a level of from about 1.5 to about 15% by weight of said emulsion.

19. The emulsion of claim 18 wherein said water is present at a level of from about 65 to about 95.5% by weight.

20. The emulsion of claim 11 having a pH within the range of about 3 to about 5 and a viscosity within the range of about 0.5 to about 2 Pa.s as measured at 20° C. and at a shear rate of about 3 to about 6 cm$^{-1}$.

21. The emulsion of claim 11 further containing one or more of the following additives:
    (f) 0.05 to 1.5% by weight of one or more stabilizers for hydrogen peroxide, including dipicolinic acid, quinolinic acid, polyphosphates or the acylation products of phosphorous acid;
    (g) one or more buffers for adjusting the pH value of the emulsion to from 3 to 5;
    (h) one of more active hair-cosmetic components, including water-soluble protein derivatives and water-soluble cationic polymers; and
    (i) perfumes.

22. A method for forming a hair dyeing preparation comprising thoroughly mixing the emulsion of claim 11 or claim 19 with an oil-in-water emulsion of a hair dyeing cream containing an oxidation hair dye precursor, said emulsions being mixed at a weight ratio of from about 1:1 to about 1:3 respectively.

23. A method for forming a hair bleaching preparation comprising thoroughly mixing the emulsion of claim 11 or claim 19 with an oil-in-water emulsion of a hair bleaching cream, said emulsions being mixed at a weight ratio of from about 1:1 to about 1:3 respectively.

24. A process for dyeing hair comprising applying to the hair the mixed emulsions of claim 22 and rinsing the hair after a contact time of about 15 to about 60 minutes at room temperature.

25. A process for bleaching hair comprising applying to the hair the mixed emulsions of claim 23 and rinsing the hair after a contact time of about 15 to about 60 minutes at room temperature.

* * * * *